United States Patent

Millauer et al.

[11] Patent Number: 5,821,393
[45] Date of Patent: Oct. 13, 1998

[54] PROCESS FOR THE PREPARATION OF AROMATIC BROMOALKYL-SUBSTITUTED HYDROCARBON COMPOUNDS

[75] Inventors: Hans Millauer, Eschborn; Frank Küber, Oberursel, both of Germany

[73] Assignee: Hoechst Aktiengesellschaft, Germany

[21] Appl. No.: 769,724

[22] Filed: Dec. 18, 1996

[30] Foreign Application Priority Data

Dec. 18, 1995 [DE] Germany ............... 195 47 249.7

[51] Int. Cl.⁶ .................. C07C 22/00; C07C 17/00
[52] U.S. Cl. ............. 570/196; 204/157.94; 204/157.99; 204/158.1
[58] Field of Search ............... 204/157.94, 157.99, 204/158.1; 570/144, 191, 196, 197

[56] References Cited

U.S. PATENT DOCUMENTS

| | | | |
|---|---|---|---|
| 3,190,825 | 6/1965 | Huyser | 570/196 |
| 4,165,268 | 8/1979 | Marti et al. | 204/157.99 |
| 4,188,342 | 2/1980 | Chupp | 260/578 |
| 4,252,624 | 2/1981 | Marti et al. | 204/158 A |
| 4,302,306 | 11/1981 | Katsuragawa et al. | 204/158 HA |
| 4,923,580 | 5/1990 | Turner et al. | 204/157.99 |
| 5,502,261 | 3/1996 | Millauer | 570/196 |
| 5,527,967 | 6/1996 | Millauer | 568/17 |
| 5,599,989 | 2/1997 | Millauer | 564/290 |

FOREIGN PATENT DOCUMENTS

| | | |
|---|---|---|
| 0 675 095 | 10/1995 | European Pat. Off. . |
| 0 684 248 | 11/1995 | European Pat. Off. . |
| 0 685 456 | 12/1995 | European Pat. Off. . |
| 2 370 017 | 6/1978 | France . |
| 2 080 299 | 2/1982 | United Kingdom . |

OTHER PUBLICATIONS

M.E. Jung et al., Tetrahedron Letters 29 (1988) 6199 no month available.

P. Mazaleyrat, Chem. Commun. 1985, 317 no month available.

T. Hayashi et ak., J. Am. Chem. Soc. 110 (1988 8153) or chlorobenzene or dichloorobenzene no month available.

*Primary Examiner*—Kathryn L. Gorgos
*Assistant Examiner*—Edna Wong
*Attorney, Agent, or Firm*—Connolly & Hutz

[57] ABSTRACT

The present invention relates to a process for the preparation of an aromatic bromoalkyl-substituted hydrocarbon compound, in which an alkyl-substituted aromatic hydrocarbon compound is reacted with a brominating agent in the presence of water.

5 Claims, No Drawings

20

PROCESS FOR THE PREPARATION OF AROMATIC BROMOALKYL-SUBSTITUTED HYDROCARBON COMPOUNDS

BACKGROUND OF THE INVENTION

The present invention relates to a process for the preparation of aromatic (bromoalkyl)-substituted hydrocarbon compounds by bromination of an alkyl-substituted hydrocarbon compound with a brominating agent in the presence of water and, if appropriate, an organic solvent and, if appropriate, a reducing agent.

Aromatic (bromoalkyl)-substituted hydrocarbon compounds are important intermediate products in the synthesis of organic compounds, in particular for the preparation of active compounds for pharmaceutical products, plant protection agents and numerous other intended uses.

Thus, for example, 2,2'-bis(bromomethyl)-1,1'-binaphthyl is a valuable intermediate product for the preparation of a number of bifunctional organic compounds which can be converted, for example, into alcohols, esters, amines, quaternary ammonium salts, phosphines or phosphinous acid esters by exchange of the bromine atoms. or example, 2,2'-bis-(bromomethyl)-1,1'-binaphthyl is a central intermediate product in the preparation of 2,2'-bis-[(diphenylphosphino)-methyl]-1,1'-binaphthyl (NAPHOS) and other bidentate phosphorus ligands. According to JP-A 79/39059, NAPHOS is obtained by reaction of 2,2'-bis-(bromomethyl)-1,1'-binaphthyl with diphenylphosphinous acid methyl ester and subsequent reduction with trichlorosilane. According to German Patent Applications EP-A-684 248 and EP-A685 456, NAPHOS is prepared starting from 2,2'-bis-(bromomethyl)-1,1'-binaphthyl by quaternization twice with trimethylamine and subsequent reaction with magnesium diphenyl-phosphide. NAPHOS or water-soluble polysulfonates (BINAS) prepared therefrom can be used as ligands for the preparation of complexes of certain heavy metal atoms. Water-soluble complexes of BINAS with rhodium, for example, are employed as catalysts for the process, carried out on a large industrial scale, of hydroformylation of olefins, in particular of propylene ("oxosynthesis").

Another industrially important bromomethyl compound is 2-(bromomethyl)-biphenyl, which is required for the synthesis of indene compounds. For example, 2-methylindene is used for building up bridged ligands for novel metallocenes of zirconium, a highly active class of catalysts for olefin polymerization.

Methyl-substituted aromatic hydrocarbons can be brominated selectively on the methyl group with N-bromosuccinimide. Numerous processes of this type are described. A summary is found in "Methoden der Organische Chemie" [Methods of Organic Chemistry] (Houben-Weyl), 4th Edition, Volume V/4, pages 341 et seq. Carbon tetrachloride or other chlorinated solvents are chiefly used as the solvents. The preparation of 2,2'-bis-(bromomethyl)-1, 1'-binaphthyl has also been described in several instances. It is carried out by bromination of 2,2'-dimethyl-1,1'-binaphthyl with N-bromosuccinimide in the presence of an agent which forms free radicals and/or under irradiation with short wavelength light by means of a UV lamp. Solvents which are employed here are compounds which are inert under the reaction conditions and suppress bromination of the nucleus, such as carbon tetrachloride (M. E. Jung et al., Tetrahedron Letters 29 (1988) 6199; H. J. Bestmann et al., Chem. Ber. 107 (1974) 2926; P. Mazaleyrat, Chem. Commun. 1985, 317; T. Hayashi et al., J. Am. Chem. Soc. 110 (1988) 8153) or chlorobenzene or dichlorobenzene (EP-A-675 095).

The presence of non-polar solvents has been recommended to date during brominations of alkyl-substituted aromatic hydrocarbon compounds (J. March, Advanced Org. Chemistry, 4th Edition., 1992, pages 695). One disadvantage of this process is that by-products formed during the bromination, for example succinimide, are obtained as a solid and are deposited on the cooler parts of the apparatus, for example on the surfaces of heat exchangers. This impedes removal of heat from the reaction medium, which can lead to an undesirable increase in temperature. In photoinitiated processes, the formation of deposits on the immersed tube of the UV lamp and interference in the introduction of light can additionally occur as a result of a lack of removal of heat.

When the processes described in the prior art are applied on an industrial scale, a further deficiency often also emerges: if starting compounds prepared on a semi-industrial or industrial scale (technical grade) are employed, the bromination with N-bromosuccinimide is sometimes inhibited considerably. In particular, the bromination of the compounds 2,2'-dimethyl-1,1'-binaphthyl or 2-methylbiphenyl, which, because of their customary mode of preparation (reductive coupling of an aromatic Grignard compound with an aromatic bromine compound with catalytic additions of certain metal compounds), still contain traces of these metals, such as palladium or nickel, often requires very long reaction times. It is thus found, for example, that in the case of 2,2'-dimethyl-1,1'-binaphthyl a longer induction period initially occurs after addition of the brominating agent before the bromination reaction starts. A severe delay in the reaction can also occur in the subsequent course of the bromination, which results in reaction times of 5 to 8 hours or longer (EP-A-675 095).

DETAILED DESCRIPTION OF THE INVENTION 2,2'-Dimethyl-1,1'-binaphthyl, which is alternatively obtained by oxidative coupling by the electrochemical process according to EP-A-0 663 378, can also contain severely inhibiting substances as a result of its preparation.

The measures usually implemented, such as high irradiation outputs or higher concentrations of agents which form free radicals, larger excesses of brominating agent (for example N-bromosuccinimide) and/or long reaction times are capable only of partly solving the problem of inhibition, without eliminating its causes.

For these reasons, the processes described are unsuitable for an economical operating procedure on an industrial scale.

It was desirable to develop a process which avoids industrial problems during the process and delays in the reaction.

There was therefore the object of providing a process by which aromatic (bromoalkyl)-substituted hydrocarbon compounds can be prepared on an industrial scale with high space/time yields and under high safety standards. This object is achieved by the process according to the invention.

The present invention thus relates to a process for the preparation of an aromatic (bromoalkyl)-substituted hydrocarbon compound in which an alkyl-substituted aromatic hydrocarbon compound is reacted with a brominating agent in the presence of water.

Examples of aromatic (bromoalkyl)-substituted hydrocarbon compounds which are obtainable by the process according to the invention are mono- or polynuclear aromatics which carry one or more (bromoalkyl) substituents. The bromoalkyl substituents preferably have 1 to 10 carbon atoms and one or more bromine atoms. Bromomethyl is particularly preferred. Bromine atoms can also be carried on two alkyl substituents which are bonded to one another to form a ring. Examples of aromatic (bromoalkyl)-substituted hydrocarbon compounds are 2,2'-bis-(bromomethyl)-1,1'-binaphthyl, 2-(bromomethyl)-biphenyl, 1,2-dibromoacenaphthene, o-(bromomethyl)-toluene, m-(bromomethyl)-toluene, p-(bromomethyl)-toluene, benzyl bromide, benzal bromide, o-chlorobenzyl bromide, m-chlorobenzyl bromide, p-chlorobenzyl bromide, o-bromobenzylbromide, m-bromobenzyl bromide or p-bromobenzyl bromide.

The term alkyl-substituted aromatic hydrocarbon compound is understood as meaning, for example, mono- or polynuclear aromatics which carry one or more alkyl substituents. The alkyl substituents preferably contain 1 to 10 carbon atoms, and methyl is particularly preferred. It is also possible for two alkyl substituents to be bonded with one another to form a ring. In addition to the alkyl substituents, the alkyl-substituted aromatic hydrocarbon compound can also carry further substituents, such as halogen atoms. Examples of alkyl-substituted aromatic hydrocarbon compounds are toluene, o-xylene, m-xylene, p-xylene, 2,2'-dimethyl1,1'-binaphthyl, 2-methylbiphenyl, acenaphthene, o-chlorotoluene, m-chlorotoluene, p-chlorotoluene, o-bromotoluene, m-bromotoluene or p-bromotoluene.

Brominating agents are understood as meaning all compounds which are capable of brominating alkyl-substituted aromatic hydrocarbon compounds. N-bromosuccinimide, N-bromophthalimide or 1,3-dibromo-5,5-dimethylhydantoin are preferred.

If compounds which are not liquid at the chosen reaction temperature or which give bromination products which are not liquid at the chosen reaction temperature are employed as starting substances, the process according to the invention is preferably carried out in the presence of an organic solvent.

Preferred organic solvents are those which are inert or largely inert under the reaction conditions and are immiscible with water or water-miscible to only a slight extent, i.e. compounds which have a non-polar or only slightly polar character. Organic solvents which are usually employed are mono- or polyhalogenated, in particular -chlorinated, aliphatic or aromatic hydrocarbons, such as methylene chloride, chloroform, carbon tetrachloride, 1,2-dichloroethane, chlorobenzene, 1,2-1,3- or 1,4-dichlorobenzene or mixtures of the solvents mentioned. Fluorochlorohydrocarbons, such as 1,1,2-trichlorotrifluoroethane, can also furthermore be used as organic solvents.

If an organic solvent is employed, the lower limit of the amount is preferably chosen such that both the alkyl-substituted aromatic hydrocarbon compound to be reacted and the bromination product obtained therefrom dissolve completely therein. The upper limit is not critical. In general, it is sufficient to use a weight ratio of the alkyl-substituted aromatic hydrocarbon compound to the organic solvent of about 1:(1 to 20), preferably 1:(3to 10).

The minimum amount of the water employed in the process according to the invention is chosen such that by-products formed (for example succinimide) are either completely dissolved therein or are dissolved to an extent such that the undissolved portion can cause no impairment in the course of the reaction. In general, the weight ratio of the brominating agent (for example N-bromosuccinimide) to water is about 1:(1 to 20), preferably 1:(1.5 to 5).

In a preferred embodiment of the process according to the invention, a reducing agent is added to the reaction mixture. Examples of reducing agents are reducing compounds of sulfur or phosphorus in its low oxidation levels, for example salts such as sulfites, hydrogen sulfites, bisulfites, dithionites, thiosulfates, hypophosphites or phosphites; reducing nitrogen compounds, for example hydroxylamine or hydrazine, are furthermore suitable. Reducing metal ions, for example iron(II) or titanium(III) compounds, are likewise suitable. The molar ratio of the reducing agent to the alkyl-substituted aromatic hydrocarbon compound is (0.001 to 0.1):1, preferably (0.005 to 0.05):1.

The process according to the invention is preferably carried out under irradiation with short wavelength light and/or in the presence of an agent which forms free radicals. Light sources which can be used are customary sources of radiation with an adequate content of short wavelength daylight or ultraviolet radiation, in particular in the spectral range from about 250 to 500 nanometers.

If the process according to the invention is carried out in the presence of an agent which forms free radicals, customary agents which form free radicals, such as peroxo compounds, for example dialkyl peroxides, diacyl peroxides, alkyl hydroperoxides, percarboxylic acids, peroxo compounds of inorganic acids or organic azo compounds, can be employed.

The agents which form free radicals and are added if appropriate are added in the customary weight ratios of about 0.1 to 5, preferably 0.5 to 2%, based on the educt. The combination of irradiation and addition of agents which form free radicals can also be used in the process according to the invention.

The process according to the invention is carried out at temperatures from −10° C. to 100° C., preferably from 10° C. to 70° C., and particularly preferably from 20° C. to 50° C.

If an organic solvent has been employed in the process according to the invention, it is preferable to separate the aqueous phase from the organic phase for working up the reaction mixture. It may be expedient for this purpose first to increase the temperature of the reaction mixture still further, in order to dissolve any amounts of suspended reaction product (for example succinimide). The subsequent working up steps then proceed in a manner known per se, for example by removal of the solvent by distillation and subsequent distillation or recrystallization of the product.

The bromination reaction in the process according to the invention proceeds swiftly and without noticeable side reactions. For introduction of one bromine atom, about one mol of brominating agent (for example N-bromosuccinimide) is required per mole of educt. For monobrominations, the educt and the brominating agent (for example N-bromosuccinimide) are therefore employed in a molar ratio of 1:(0.8 to 1.2), preferably 1:(0.9 to 1.1), and particularly preferably 1:(0.95 to 1.05). In the case of dibrominations, the educt and the brominating agent (for example N-bromosuccinimide) are employed in a molar ratio of 1:(1.6 to 2.4), preferably 1:(1.8 to 2.2), and particularly preferably 1:(1.9 to 2.1).

The process according to the invention can be carried out by initially introducing the alkyl-substituted aromatic hydrocarbon compound and water and, if appropriate, an organic solvent and/or a reducing agent into the reaction vessel and mixing them with one another by stirring. The brominating agent, for example N-bromosuccinimide, can be added to this mixture all at once or in portions. The bromination can be started by irradiating the reaction mixture with a suitable light source and/or adding an agent which forms free radicals and bringing the mixture to the reaction temperature.

In the case of addition of the brominating agent (for example N-bromosuccinimide) in portions, the rate of metering is matched to the course of the reaction. Indications of the course of the reaction are obtained, for example, by determining the temperature course or by recording the current concentration of the brominating agent (for example N-bromosuccinimide) by analysis.

The process according to the invention allows the preparation of aromatic (bromoalkyl)-substituted hydrocarbon compounds, in particular with an increased space/time yield. The examples which follow serve to illustrate the invention, but have no limiting character at all.

EXAMPLE 1

A cylindrical 2 liter glass vessel with a glass cooling jacket and a bottom drain tap is used. The vessel is equipped with a stirrer, a filling connector for introduction of N-bromosuccinimide and a thermocouple, connected to a digital display (sensitivity 0.1° C.) and temperature recorder. The cooling jacket is connected to a thermostat with water which can be temperature-controlled at a constant ±0.1° C. Irradiation is carried out externally through the glass jacket of the reactor by means of a daylight lamp ("VITALUX", 300 watt), which is positioned 60 mm from the glass jacket of the reactor.

212 g (0.75 mol) of 2,2'-dimethyl-1,1'-binaphthyl, 900 ml of chlorobenzene, 450 ml of water, 68 g (0.38 mol) of N-bromosuccinimide and 0.52 g (0.005 mol) of sodium hydrogen sulfite are initially introduced into the reactor.

The mixture is brought to a temperature of 19°–20° C. while stirring vigorously (the temperature of the cooling brine is constantly 18.0° C. throughout the entire duration of the experiment). The air is displaced from the reactor by passing in nitrogen and covering the mixture with a layer of nitrogen, and the irradiation is started. After an induction period of about 5 to 10 minutes, the reaction starts, the temperature increasing by about 5°. Immediately after the temperature starts to fall again, a further 68 g of N-bromosuccinimide are introduced. After again waiting for the temperature to reach the maximum, a further 67 g of N-bromosuccinimide, and thereafter further portions of 34 g, then 30 g and finally 8 g of N-bromosuccinimide, are introduced. The last portion is added on average about 1 hour after the start of the irradiation. A total of 275 g (1.55 mol) of N-bromosuccinimide are employed. After a total of 2 hours, the irradiation is ended. The reaction mixture is then heated to 40° C. and the two liquid phases are separated. The chlorobenzene phase is washed once with 450 ml of water and then evaporated under reduced pressure. The distillation residue, which comprises a brownish solid, is stirred with 800 ml of hot methanol and filtered off with suction, and the filter cake is washed with 200 ml of methanol and dried. The yield is 290 g (88%) of 2,2'-bis-(bromomethyl)-1,1'-binaphthyl. HPLC analysis (column: Hypersil; eluent: n-hexane/methylene chloride 96:4; flow rate: 1.5 ml/minute) shows the following composition of the product: 84% of 2,2'-bis-(bromomethyl)-1,1'-binaphthyl, 4% of 2-(bromomethyl)-2'-methyl-1,1'-binaphthyl, 10% of 2-(bromomethyl)-2'-(dibromomethyl)-1,1'-binaphthyl and 2% of unknown substances.

EXAMPLE 2

336 g (2.0 mol) of 2-methylbiphenyl (technical grade, purity 89%), 700 ml of chlorobenzene, 600 ml of water, 366 g (1.03 mol) of N-bromosuccinimide and 1.9 g (0.01 mol) of sodium pyrosulfite, $Na_2S_2O_5$, are initially introduced into a test apparatus as described in Example 1.

The mixture is brought to a temperature of 24°–25° C. while stirring vigorously (the temperature of the cooling brine is constant at 23.0° C. throughout the entire duration of the experiment). The air is displaced from the reactor by passing in nitrogen and covering the mixture with a layer of nitrogen, and the irradiation is started. After an induction period of about 20 minutes, the reaction starts, the temperature increasing by about 3°–40°. After a total of 3 hours, the irradiation is ended. The reaction mixture is then heated to 35° C. and the two liquid phases are separated. The chlorobenzene phase is washed once with 600 ml of water and then evaporated under reduced pressure. A pale brown oil which, after fractional distillation, gives 425 g of 2-(bromomethyl)-biphenyl, boiling point 128°–134° C./0.03 mbar, is obtained. The yield is 86%. According to GC analysis (apparatus: Hewlett Packard 5890 Series II; column: 30 m HPI; 80° C. (2 minutes), 10°/minute, 270° C. (15 minutes); flow rate: He, 1.0 ml/minute), the purity of the product is 89.5%.

We claim:

1. A process for the preparation of an aromatic bromoalkyl-substituted hydrocarbon compound in which an alkyl-substituted aromatic hydrocarbon compound is reacted with a brominating agent in contact with water to produce a reaction mixture which is subsequently treated to prepare the aromatic bromoalkyl-substituted hydrocaron compound, and wherein the brominating agent is selected from the group consisting of N-bromosuccinimide, N-bromophthalimide and 1,3-dibromo-5,5-dimethylhydantoin.

2. The process as claimed in claim 1, wherein the reaction mixture additionally comprises an organic solvent.

3. The process as claimed in claim 1, wherein the reaction mixture additionally comprises a free radical initiator.

4. The process as claimed in claim 1, wherein the reaction mixture is irradiated with light.

5. A process for the preparation of an aromatic bromoalkyl-substituted hydrocarbon compound in which an alkyl-substituted aromatic hydrocarbon compound is reacted with a brominating agent in contact with water to produce a reaction mixture which is subsequently treated to prepare the aromatic bromoalkyl-substituted hydrocarbon compound, and wherein the reaction mixture additionally comprises a reducing agent.

* * * * *

UNITED STATES PATENT AND TRADEMARK OFFICE
CERTIFICATE OF CORRECTION

PATENT NO. : 5,821,393
DATED : October 13, 1998
INVENTOR(S) : HANS MILLAUER ET AL It is certified that error appears in the above-identified patent and that said Letters Patent is hereby corrected as shown below:

Column 2, line 37, "DETAILED DESCRIPTION OF THE INVENTION" should be deleted and reinserted at line 53.

Column 6, line 22, "3° -40°" should read -- 3-4° --.

Signed and Sealed this

Twenty-third Day of February, 1999

Attest:

Q. TODD DICKINSON

*Attesting Officer*  *Acting Commissioner of Patents and Trademarks*